United States Patent [19]

Michaelis et al.

[11] Patent Number: 5,795,858
[45] Date of Patent: Aug. 18, 1998

[54] TREATMENT OR PREVENTION OF CROHN'S DISEASE AND/OR ULCERATIVE COLITIS

[75] Inventors: Jurgen Michaelis, Kariong; Merilyn J. Sleigh, North Sydney, both of Australia

[73] Assignee: Peptide Technology Limited, New South Wales, Australia

[21] Appl. No.: 403,718

[22] PCT Filed: Sep. 26, 1994

[86] PCT No.: PCT/AU94/00575

§ 371 Date: Mar. 31, 1995

§ 102(e) Date: Mar. 31, 1995

[87] PCT Pub. No.: WO95/08339

PCT Pub. Date: Mar. 30, 1995

[30] Foreign Application Priority Data

Sep. 24, 1993 [AU] Australia ................... PM1448

[51] Int. Cl.$^6$ .................................................. A61K 38/00
[52] U.S. Cl. ........................... 514/8; 514/9; 514/11; 514/15; 514/16; 514/17; 514/18; 530/328; 530/329; 530/330
[58] Field of Search ................. 514/8, 9, 11, 15–18; 530/328, 329, 330

[56] References Cited

FOREIGN PATENT DOCUMENTS

| 0249390 | 12/1987 | European Pat. Off. . |
|---|---|---|
| 0249394 | 12/1987 | European Pat. Off. . |
| 8809338 | 12/1988 | WIPO . |

*Primary Examiner*—Cecilia J. Tsang
*Assistant Examiner*—C. Delacroix-Muirheid
*Attorney, Agent, or Firm*—Nixon & Vanderhye

[57] ABSTRACT

The present invention provides a method for the treatment or prevention of Crohn's disease and/or ulcerative colitis. The method involves the administration of Peptide T or its derivatives or analogues. Preferred compounds used in the method include:

1. D—Ala—Ser—Thr—Thr—Thr—Asn—Tyr—Thr—NH$_2$
2. Ala—Ser—Thr—Thr—Thr—Asn—Tyr—Thr
3. D—Ala—Ser—Thr—Thr—Thr—Ans—Tyr—Thr
4. D—Ala—Ala—Ser—Ser—Ser—Asn—Tyr—Met
5. Thr—Asp—Asn—Tyr—Thr
6. Thr—Thr—Ser—Tyr—Thr
7. Thr—Thr—Asn—Tyr—Thr
8. D—Thr—Thr—Tyr—D—Thr
9. D—Ala—Ser—D—Thr—Thr—D—Thr—Asn—Tyr—D—Thr—NH$_2$
10. D—Ser—Ser—D—Thr—Thr—D—Thr—Thr—Tyr—D—Thr—NH$_2$

7 Claims, 7 Drawing Sheets

5,795,858

TREATMENT OR PREVENTION OF CROHN'S DISEASE AND/OR ULCERATIVE COLITIS

The present invention relates to the treatment or prevention of Crohn's Disease and/or ulcerative colitis.

BACKGROUND OF THE INVENTION

Crohn's Disease, or Regional Ileitis, is the term applied to a condition in which there is an inflammation of an area of the small intestine. This is usually accompanied by colicky abdominal pain, irregularity of the bowels, loss of weight and slight fever. The abdomen is generally distended and the thickened intestine may be felt. The narrowed intestinal canal may become obstructed, necessitating immediate operation. The cause of the disease is unknown. The primary lesion is hyperplasia of the lymph tissue in the submucosa of the intestine and in the lymph glands.

As the cause is not known, there is as yet no specific treatment. In the early stages, current treatment (or at least management) is medical, including a high-vitamin, low-residue diet, sulphonamides and antibiotics. Promising results have been reported from the use of corticosteroids in some cases. Operation, consisting of removal of the damaged section of gut, is reserved for cases which do not respond to medical treatment. Even in cases apparently successfully operated on, recurrence tends to occur in 15 percent or more of cases.

Short of surgery, therefore, corticosteroid therapy is to date the most successful remedial treatment for Crohn's Disease. However, steroid chemotherapy is not without its drawbacks and hazards. Goodman and Gilman state, in "The Pharmacological Basis of Therapeutics", Seventh Edition, 1985:

"In clinical terms, the administration of corticosteroids for their anti-inflammatory effects is palliative therapy; the underlying cause of the disease remains; the inflammatory manifestations are merely suppressed. It is this suppression of inflammation and its consequence that has made the corticosteroids such valuable therapeutic agents—indeed, at times lifesaving. It is also this property that gives them a nearly unique potential for therapeutic disaster."

Crohn's Disease is a chronic condition of the gastrointestinal tract and infects most commonly the ileum, colon or a combination of both. It is distinguished from ulcerative colitis by a differential diagnosis:

Crohn's Disease
  Acute appendicitis
  Yersinia infection
  Lymphoma
  Ulcerative jejunoileitis
Colitis
  Infective colitis
  Ischaemic colitis
  Radiation colitis
  Other causes of bleeding, e.g. colonic polyps or carcinoma.

DESCRIPTION OF THE INVENTION

It has now been discovered that a group of non-steroidal compounds, namely peptide T and its derivatives and analogues, are useful in the prevention and treatment of Crohn's Disease and/or ulcerative colitis.

Originally, many of the peptides useful in the invention were described as being effective in the prevention of infection and replication of HIV in vitro, see EP-A-0249390, EP-A-0249394 and WO-A-8809338, all of which are incorporated by reference to the maximum extent allowed by law, as are all other documents referred to in this specification. The compounds useful in the invention are also the subject of pending and as yet unpublished PCT patent application No. PCT/GB93/00649, filed 29 Mar. 1993. All compounds disclosed in these specifications are useful for the present invention. The original peptide has its basic point of origin in the octapeptide Ala—Ser—Thr—Thr—Thr—Asn—Tyr—Thr (SEQ ID NO: 1) It is called Peptide T because 50% of the amino acid residues are threonine.

Accordingly in a first aspect the present invention, consists in a method of treating or preventing Crohn's Disease and/or ulcerative colitis in a subject comprising administering to the subject a therapeutic amount of a linear or cyclic peptide of General Formula 1:

I—A—B—C—D—E—F—G—H—II (General Formula 1) (SEQ ID NO: 2)

wherein A is Ala, Gly, Val, Ser, Thr or absent,

B is Ala, Gly, Val, Ser, Thr or absent

C is Ser, Thr or absent,

D is Ser, Thr, Asn, Glu, Arg, Ile, Leu or absent,

E is Ser, Thr, Asp or absent,

F is Thr, Ser, Asn, Arg, Gln, Lys, Trp or absent,

G is Tyr, Phe, Trp, Leu, Met, Ile or absent,

H is Thr, Arg, Gly, Met, Met(O), Cys, Thr, Gly or absent,

I is Cys or absent,

II is Cys or absent, at least one of the amino acids optionally being substituted by a monomeric or polymeric carbohydrate or derivative thereof, such substitution being accomplished through hydroxyl and/or amino and/or amido groups of the amino acids, and wherein the peptide comprises at least four amino acid residues, or a pharmaceutically acceptable salt thereof.

Each of the amino acids referred to in General Formula 1 may be in the L- or D-stereoisomeric configuration and candidates for H may be esterified or amidated. The peptide comprises at least 4 amino acids.

Tetra-, penta-, hexa-, hepta-, octa- and non-peptides useful in the invention are all of the peptides chosen from the sequence:

I—A—B—C—D—E—F—G—H—II by deleting residues, for example, one at a time, from either the carboxyl or amino terminal, or from within the sequence.

It is appreciated that peptides having the core sequence of the Thr—Thr—Asn—Tyr—Thr— (SEQ ID NO: 3) may have at both ends additional amino acid residues, some of which are represented by General Formula 2:

X—Ser—Thr—Thr—Thr—Asn—Tyr—Y (General Formula 2) (SEQ ID NO: 4)

wherein X is an amino acid terminal residue selected from Ala and D-Ala and Y is a carboxy terminal residue selected from Met, Thr and Thr-amide.

A particular preferred peptide of the group of peptides has the aforementioned core sequence of —Thr—Thr—Asn—

Tyr—Thr—. These peptides of the above General Formula 2, and in particular a variant Peptide T of the formula —Ser—Thr—Thr—Thr—Asn—Tyr—(SEQ ID NO: 5), were found to be very useful in inhibiting binding of the human immunodeficiency virus (HIV) to human cells by blocking receptor sites on the cell surfaces. The term Peptide T is used throughout the specification to reference, unless the context otherwise requires peptides of General Formula 2 which all include the core peptide sequence. It is therefore intended that Peptide T encompass all of the compounds of General Formula 2 where it is understood that all such compounds are variants of the normally understood octapeptide T, also referred to as prototype Peptide T, of the particular formula D—Ala—Ser—Thr—Thr—Thr—Asn—Tyr—Thr—amide.

The invention may be useful in both clinical (human) and veterinary medicine. The invention therefore has application in a method for treating or preventing Crohn's Disease and/or ulcerative colitis, the method comprising administering to a human or other animal subject, for example on a repeated basis, a peptide of General Formula 1. The peptide will generally be administered in an effective, non-toxic amount or in such an amount that strikes an acceptable balance between efficacy and toxicity, having regard to the circumstances of the case.

Preferred peptides useful in the invention have as their active portion, an amino acid sequence of the formula:

—Thr—Thr—Asn—Tyr—Thr—

Most preferred peptides useful in the invention are the following:
1. D—Ala—Ser—Thr—Thr—Thr—Asn—Tyr—Thr—NH$_2$ (prototype Peptide T)
2. Ala—Ser—Thr—Thr—Thr—Asn—Tyr—Thr (SEQ ID NO: 6)
3. D—Ala—Ser—Thr—Thr—Thr—Asn—Tyr—Thr
4. D—Ala—Ala—Ser—Ser—Ser—Asn—Tyr—Met
5. Thr—Asp—Asn—Tyr—Thr (SEQ ID NO: 7)
6. Thr—Thr—Ser—Tyr—Thr (SEQ ID NO: 8)
7. Thr—Thr—Asn—Tyr—Thr
8. D—Thr—Thr—Tyr—D—Thr
9. D—Ala—Ser—D—Thr—Thr—D—Thr—Asn—Tyr—D—Thr—NH$_2$
10. D—Ser—Ser—D—Thr—Thr—D—Thr—Thr—Tyr—D—Thr—NH$_2$ Quite often it may be an advantage to have the amino terminal amino acid as a D-steroisomer, to protect the molecule from degradation from aminopeptidases; alternatively or additionally, the carboxy terminal amino acid may be an amino acid amide to protect the molecule from degradation from carboxypeptidases. In this connection, compounds 5, 6 and 7 listed above, include analogues with D—Thr as the amino terminal residue and/or an amide derivative at the carboxy terminal.

Furthermore, it should be understood that one more of the amino acids in the peptides may be substituted N-alkyl (e.g. ($C_1$–$C_4$) alkyl) amino acids instead of primary amino acids; examples include methyl and ethyl. The hydroxyl group side chains of one or more of the amino acids (Ser, Thr, Tyr) may be derivatised into an ether or ester group. Any (optionally substituted) alkyl ester or ether may be formed, such as ($C_1$–$C_4$) alkyl, aryl or aryl ($C_1$–$C_4$) alkyl esters, ethers, thioesters and thioethers, for example phenylester, benzylether or thiophenol ethylester. The presently preferred ethers are methyl, ethyl and propyl ethers and presently preferred esters are methyl, ethyl and propyl esters.

Furthermore, it should be understood that the C-terminal amide may be an alkyl amide with $C_1$–$C_6$ (linear, branched, or cyclic), the alkyl residue itself can be substituted with single or multiple groups such as hydroxy, fluoro, etc. Similarly, the N-terminal amino group may be acetylated with carboxylic acids of $C_1$–$C_6$ (linear, branched, or cyclic) which may be substituted with single or multiple groups such as hydroxy, fluoro, etc. Such derivations are to improve properties such as solubility, bioavailability and stability (physical, chemical, metabolic) rather than biological activity.

The hydroxyl side chains of the amino acids Ser, Thr and/or Tyr and the amido groups of the amino acids Asn and/or Gln may be substituted with different carbohydrates or derivatives of carbohydrates. Carbohydrate derivatives may be as discussed above.

Linear peptides useful in this invention may be prepared by any suitable process, such as conventional solid phase peptide synthetic techniques, see "Solid Phase Peptide Synthetic Techniques", 2nd Ed. J. M. Stewart, J. D. Young, Pierce Chemical Company, 1984, ISBN: 0-935940-03-0. A frequently used solid phase method is the Merrifield technique. Another possibility is solution phase techniques. The preferred peptide, prototype peptide T, is readily obtainable from Peptech (Europe), Hillerod, Denmark.

Cyclic peptides useful in the invention may be prepared by known techniques, such as, for example, described in Y. Hamada in *Tetrahedron Letters*, 26 5155 (1985). Cyclic peptides may be established in the form of a disulphide bridge between two Cys residues and/or by reacting the carboxy terminal amino acid residue with the amino terminal residue and/or by reacting the amino terminal residue with for example the (insert y)-carboxyl group of Glu, when Glu is at position D.

Carbohydrate derivatives may be prepared by methods known in the art. Glycosylated Peptide T is disclosed in Urge et al, *Biochem. Biophys. Res. Comms.* 184(2) 1125–1132 (1992), published 30 Apr. 1992, but the utility of the present invention is neither disclosed nor suggested.

Peptides useful in the invention may be administered as a composition in conjunction with a pharmaceutically acceptable carrier.

The peptides or peptide formulations may be used alone or in combination with any other pharmaceutically active compound, such as an anti-infective agent, for example an antibiotic and/or antiviral agent and/or antifungal agent, or another pharmaceutically active compound, such as an anti-inflammatory agent or an anti-neoplastic agent.

The peptides may be administered orally, buccally, parenterally, rectally, vaginally, by intranasal inhalation spray, by intrapulmonary inhalation or in other ways. In particular, the peptides according to the invention may be formulated for inhalation with spray or powder, for injection (for example subcutaneous, intramuscular, intravenous, intra-articular or intracisternal injection), for infusion or for oral administration and may be presented in unit dose form in ampoules or tablets or in multi-dose vials or other containers with an added preservative. The compositions may take such forms as suspensions, solutions, or emulsions or gels in oily or aqueous vehicles, and may contain formulatory agents such as suspending, stabilising and/or dispersing agents. Alternatively, the active ingredient may be in powder and/or lyophilised form for direct administration or for constitution with a suitable vehicle (e.g. sterile, pyrogen-free water, normal saline or 5% dextrose) before use. The pharmaceutical compositions containing peptide (s) may also contain other active ingredients such as antimicrobial agents, or preservatives.

The compositions may contain from 0.001–99% (w/v or, preferably, w/w) of the active material. Peptide T obtainable from Peptech (Europe) is usually formulated and packaged in a sterile manner in 5% dextrose solution in multi-dose vials. It will be appreciated that the peptide may be packaged in other carriers, such as saline.

Preferably, the concentration of peptide in each dose is in the order of 8.5 mg/ml for subcutaneous injection in one ml doses.

The compositions are administered in therapeutically or prophylactic effective doses, i.e. 0.05–10000 mg of peptide per day, in particular 5–1000 mg per day. Very large doses may be used as the peptide according to the invention is non-toxic. However, normally this is not required. The dose administered daily of course depends on the degree of control required.

For administration by injection or infusion of the composition, the daily dosage, as employed for treatment of adults of approximately 70 kg of body weight, will often range from 0.2 mg to 20 mg of active material which may be administered in the form of 1 to 4 doses over each day, such dosage ranges depending upon the route of administration and the condition of the patient.

Composition as described above may be prepared by mixing or otherwise bringing into association the ingredients.

Presently the principal therapeutic used in the treatment of Crohns disease is the steroid prednisone. In addition, the non-steroidal anti-inflammatory agents 5 ASA and 4 ASA are also commonly used. Given the usefulness of Peptide T and its analogues in treating Crohns disease it is believed that treatment involving Peptide T and its analogues may be a useful adjunct to therapy involving the use of steroidal and non-steroidal anti-inflammatories. Such as adjunct therapy may allow a reduction in the levels of administration of the commonly used anti-inflammatory agents. It is intended that such adjunct therapy is within the scope of the present invention.

BRIEF DESCRIPTION OF THE DRAWINGS

The invention will now be described in more detail with reference to the following Examples and accompanying drawings in which.

Figure 1:
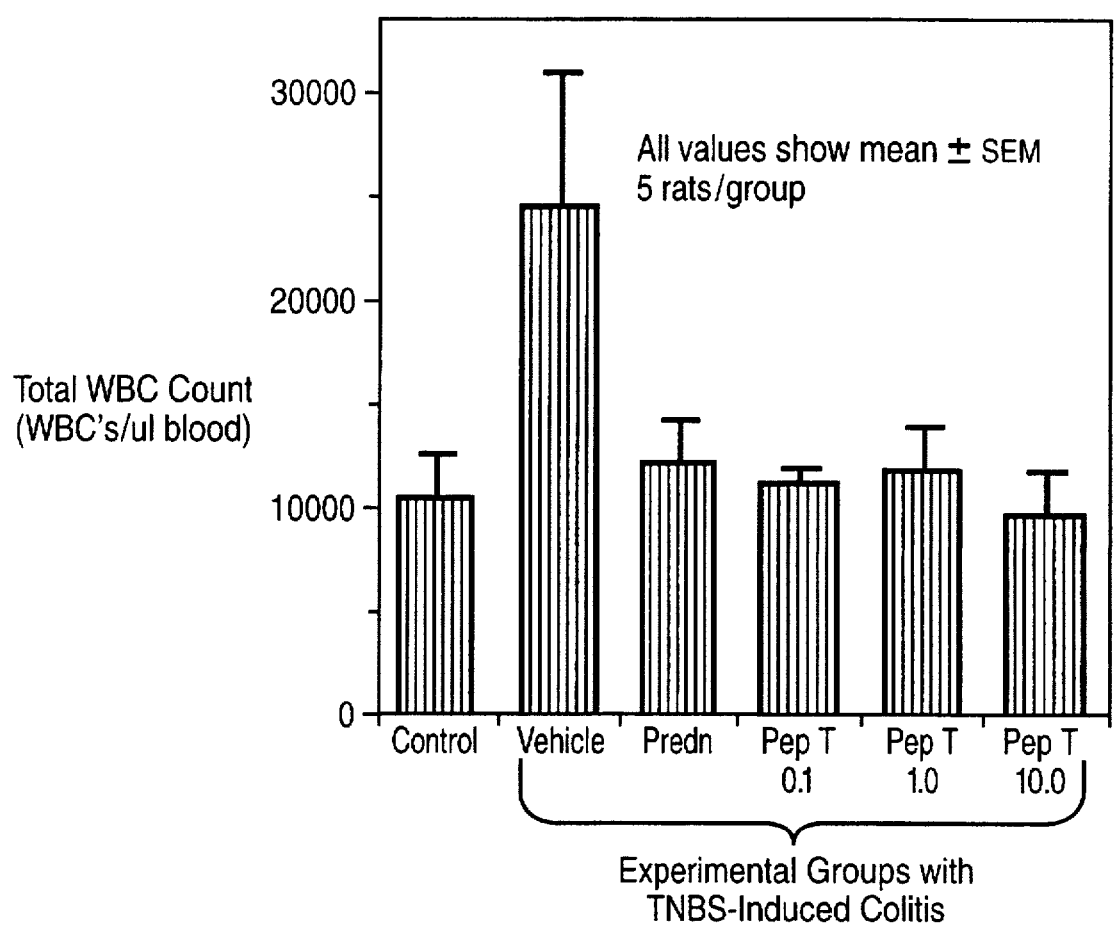
FIG. 1 shows the effects of peptide T on total WBC counts.

In order that the nature of the present invention may be more clearly understood preferred forms thereof will now be described with reference to the following examples.

EXAMPLE

A. Purpose of Study

To examine the potential therapeutic efficacy and mechanisms of action of Peptide T in the treatment of TNBS colitis in rats during both its acute/subacute (0 to 2 week) and combined acute, subacute and chronic (0 to 4 week) phases.

B. Summary of Methods

Male Sprague-Dawley rats, weighing 265–315 g were sedated with an i.p. injection of Innovar-Vet (fentanyl+ droperidol) at a dose of 0.03 ml/100 g body weight and received an intrarectal instillation of either 0.8 ml 30 mg TNBS in 30% Ethanol (TNBS colitis animals) or normal saline (control/no colitis animals). On the day following i.r. instillations, control animals were treated with a s.c. injection of vehicle and TNBS colitis animals were treated with the s.c. injection of vehicle, prednisone (5 mg/kg), or Peptide T (0.1, 1.0, 10 mg/kg). Treatment was continued on a once daily basis for the following 14 or 28 days.

On day 14 (2 week series) or 28 (4 week series), animals were weighed and anaesthetised with pentobarbital. A cardiac puncture was performed to obtain a sample of peripheral blood for the determination of total white blood cell count (WBC) using a coulter counter, and differential count. A midline laparotomy was then performed and the colon exposed and excised. The colon was then opened longitudinally and rinsed clear of fascal material. The severity of colonic mucosal injury, diarrhoea, and adhesions was then scored by an observer unaware of the treatment group of the animals using the attached criteria. The length (in cm) and weight of each colonic segment was then determined to allow the determination of the colonic weight/length ratio (as an index of intramural edema and/or fibrosis). Samples of tissue were then taken for biochemical determination of tissue myeloperoxidase (MPO) activity, as an index of granulocyte accumulation using standard biochemical techniques. Samples of tissue were also taken and fixed for subsequent processing for histopathological examination.

Differences between the different treatment groups were analysed using either one way analysis of variance (body weight, WBC counts, colonic weight/length ratio, MOP activity) or the non-parametric equivalent Kruskall-Wallis test (semiquantitive grading of severity of mucosal injury, adhesions, or diarrhoea). Significance of differences between individual pairs of treatment groups were then assessed using post hoc Tukey's test for parametric data and Dunn's multiple comparison test for non-parametric data.

| CRITERIA FOR SEMI-QUANTITATIVE GRADING OF MACROSCOPIC INJURY | |
|---|---|
| DEGREE AND TYPE OF INJURY | SCORE |
| Normal appearance | 0 |
| Focal hyperemia, no ulcers | 1 |
| Single site of limited (2–5 mm) ulceration without inflammation | 2 |
| Single site of limited (2–5 mm) ulceration with inflammation | 3 |
| Two or more sites of discrete ulceration or inflammation | 4 |
| Major site of ulceration or inflammation extending 1–2 cm along length of colon | 5 |
| Major site of ulceration or inflammation extending >2 cm along length of colon (increased by 1 for each additional cm of damage | 6–10 |
| ADHESION SCORE | |
| No adhesions | 0 |
| Limited adhesion of pericolic fat or 1–2 loops of small bowel | 1 |
| Adhesion to several (3–5) loops of small bowel +/– pericolic fat | 2 |
| Extensive adhesion of multiple loops of bowel | 3 |

C. Summary of Results of 2 Week Series Examining the Efficacy of Peptide T in the Treatment of TNBS Colitis

C.i Effects of Peptide T on Total WBC Counts

As can be seen in FIG. 1, in animals with TNBS-induced colitis receiving once daily s.c. injections of vehicle, the total WBC counts, were approximately double those observed in control (no colitis) animals receiving vehicle. Once daily s.c. injections for 2 weeks with prednisone 5 mg/kg, Peptide T 0.1 mg/kg, Peptide T 1.0 mg/kg, or Peptide T 10 mg/kg, all led to reductions in total WBC counts in animals with TNBs colitis when compared to animals with colitis receiving vehicle. Although these reductions in WBC counts did not quite attain statistical significance ($p<0.05$), all of them showed p values of 0.06–0.07 vs TNBs colitis animals receiving vehicle.

C.ii Effects of peptide T on TNBS Colitis-Associated Changes in Body Weight

Figure 2:
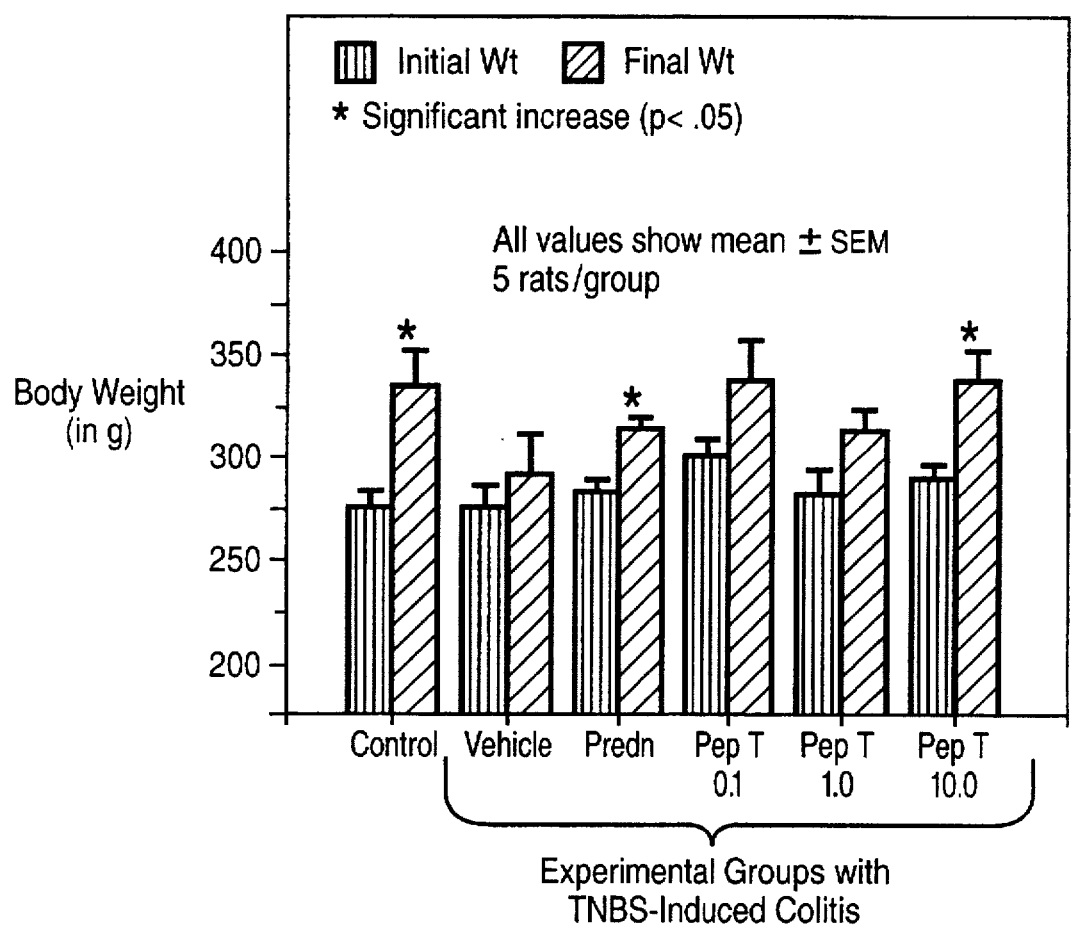
FIG. 2 shows the effects of Peptide T on TNBS colitis-associated changes in body weight.

FIGS. 2 shows the initial (i.e. prior to colitis induction) and final body weights of animals in each different treatment group 2 weeks after initiation of TNBS colitis. As can be seen, control animals (i.e. those with no colitis receiving daily injections of vehicle) experienced a significant ($p<0.05$) weight gain over the 2 week period. In contrast, animals with TNBs colitis receiving vehicle failed to gain significant body weight during the 2 week evolution of the colitis. Interestingly, treatment with either the prednisone or Peptide T at any of the 3 doses tended to cause increased weight gains in animals with colitis, with this becoming significant ($p<0.05$) in animals receiving prednisone and Peptide T at the 10 mg/kg dose [and approaching significance (p values of 0.06 to 0.08) in animals receiving Peptide T at 0.1 or 1.0 mg/kg].

C.iii Effects of Peptide T on Parameters of Colonic Injury

Figure 3:
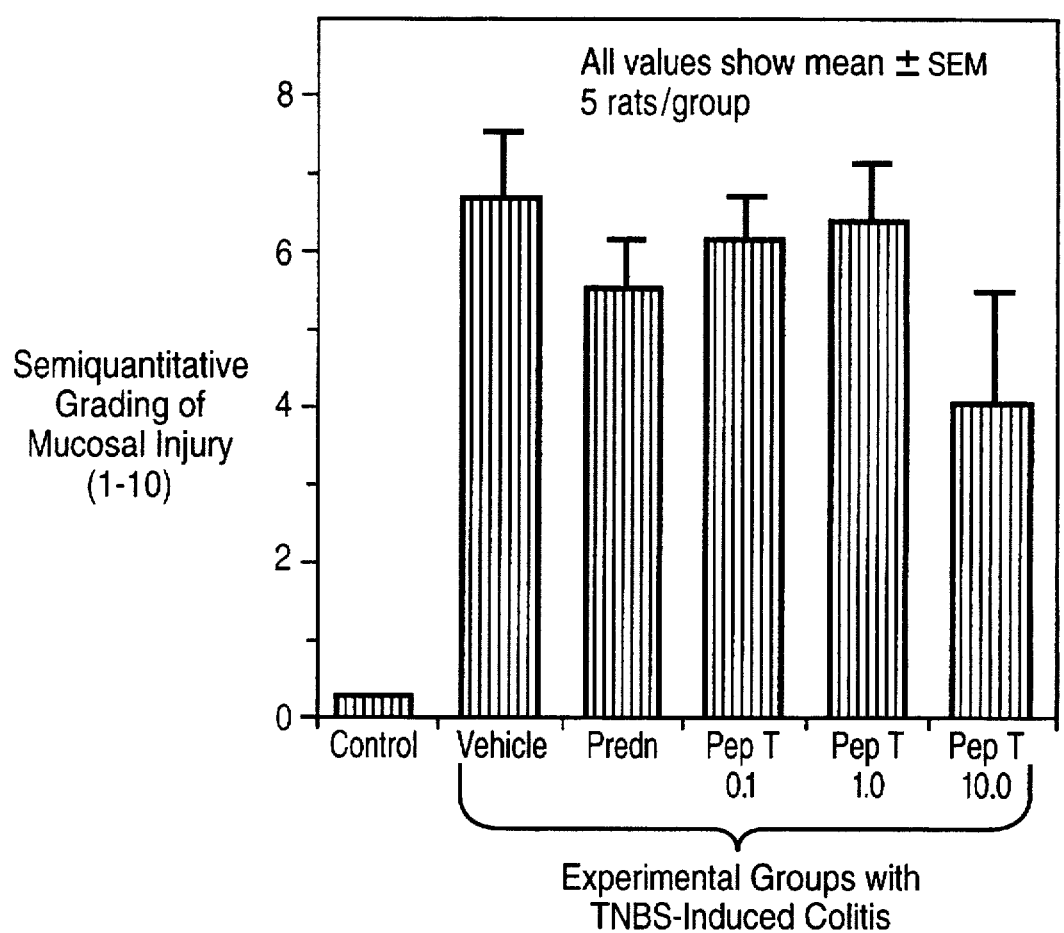
FIG. 3 shows the effects of Peptide T on the severity of mucosal injury.
Figure 4:
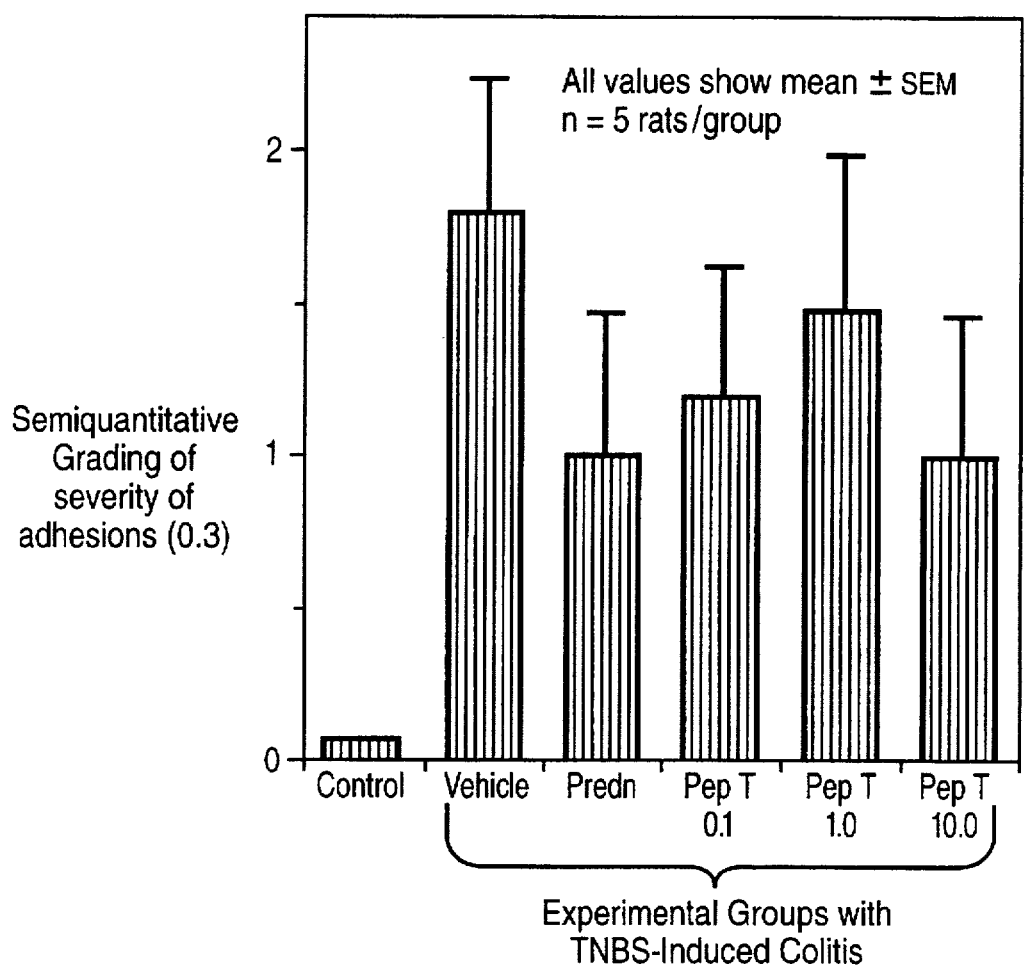
FIG. 4 shows the effects of Peptide T on the severity of colonic adhesions.
Figure 5:
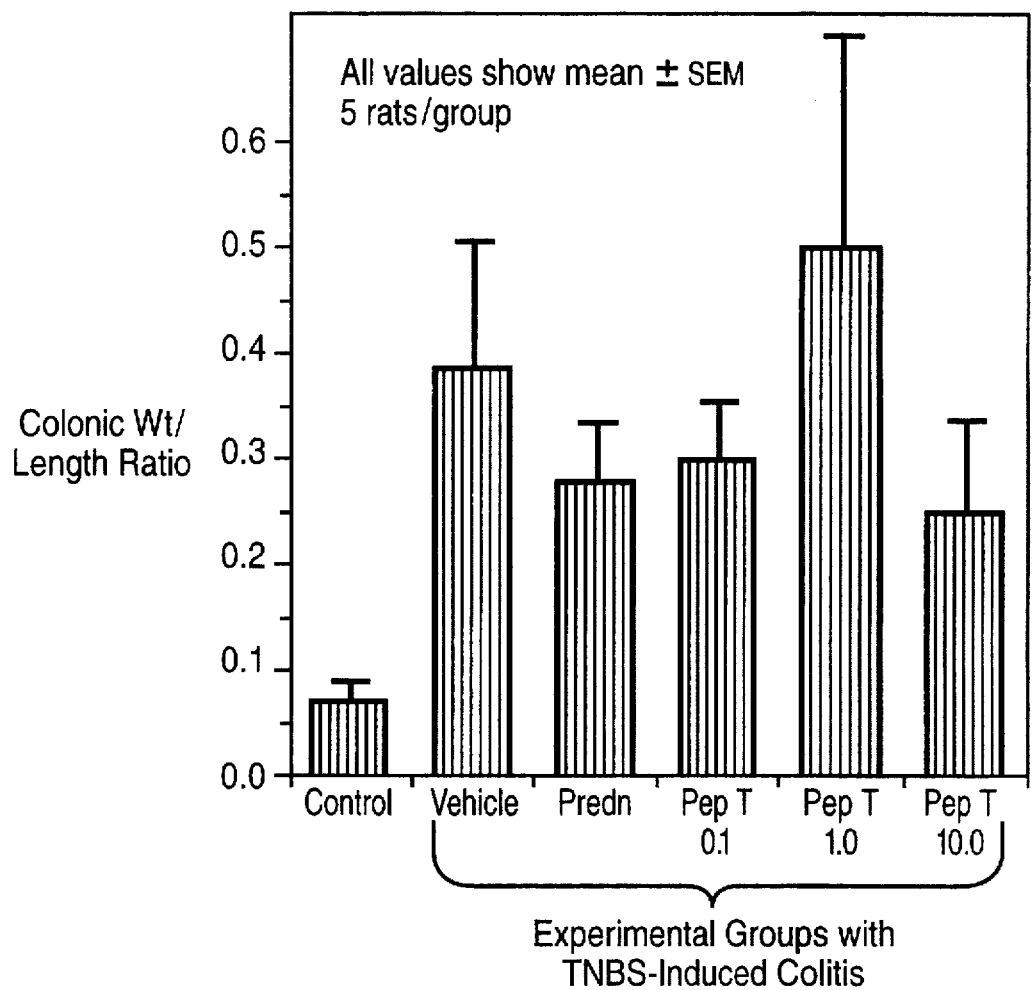
FIG. 5 shows the effects of Peptide T on colonic weight/length ratio.
Figure 6:
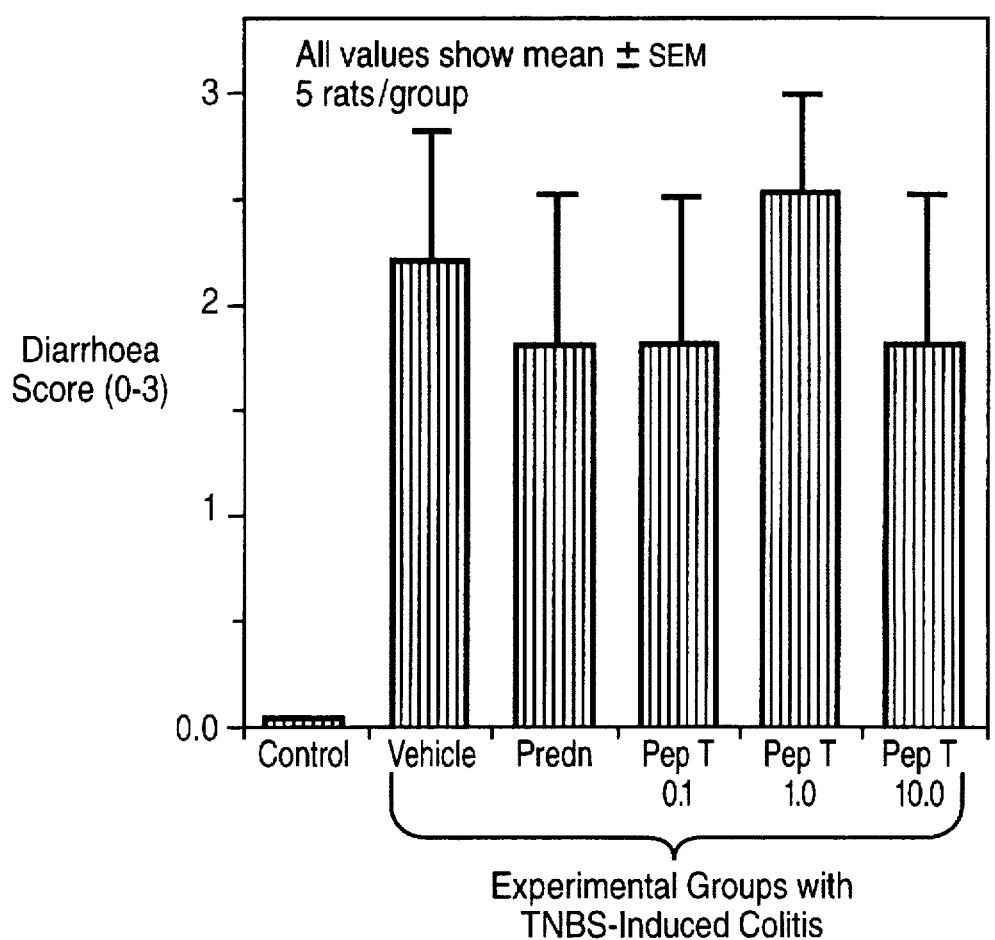
FIG. 6 shows the effects of Peptide T on degree of diarrhoea.
Figure 7:
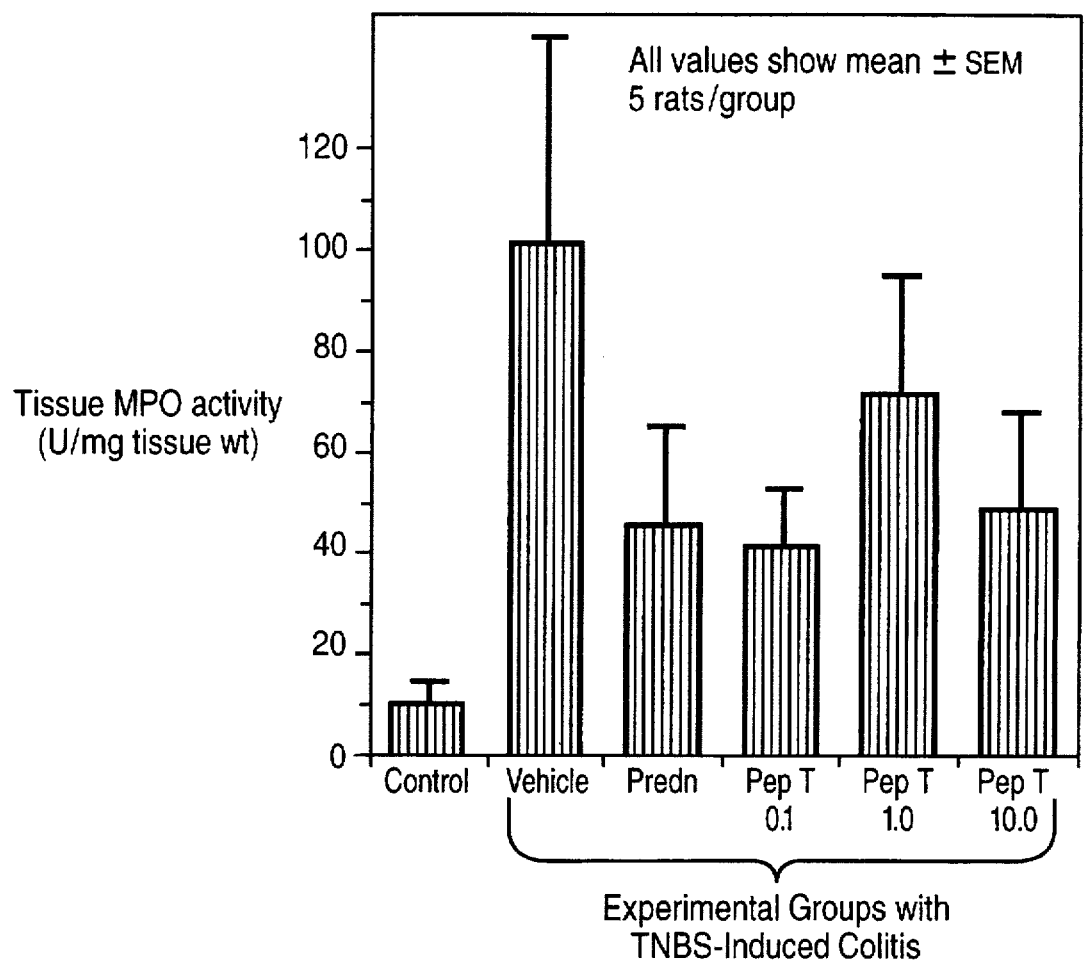
FIG. 7 shows the effects of Peptide T on colonic myeloperoxidase activity.

FIGS. 3 to 7 show results for various indices of colonic injury/colitis. As can be seen in FIG. 3, none of the treatments attenuated the severity of mucosal injury as assessed using an established semiquantitative grading scale. There was a subtle suggestion however, that Peptide T at a dose of 10 mg/kg may have marginally reduced the severity of mucosal injury. In a similar fashion, none of the treatments significantly reduced the severity of colonic adhesions (FIG. 4) developing in animals with TNBS colitis, although there was a general trend towards reduction of adhesions in animals treated with prednisone or peptide T 0.1 or 10 mg/kg. Virtually identical patterns were observed using colonic weight/length ratio (FIG. 5) and colonic myeloperoxidase activity (FIG. 7) as indices of colonic edema and granulocyte accumulation respectively. Despite these subtle trends suggesting a reduction in the severity of TNBs colitis in animals treated with prednisone or Peptide T 0.1 or 10 mg/kg, virtually all animals in the colitis groups (treated and untreated) demonstrated a similar degree of diarrhoea (FIG. 6).

C.iv Summary of Results/Conclusions for 2 Week Series

The results of assessments performed 2 weeks following induction of TNBs colitis (i.e. during the acute and subacute phase of the colitis), seems to indicate that Peptide T at any of the 3 doses (0.1, 1.0, 10 mg/kg) appears comparable to prednisone in reducing the severity of the leukocytosis and failure to thrive/lack of weight gain associated with the development of TNBS colitis in rats. These results are consistent with the hypothesis that Peptide T is reducing the constitutional or systemic manifestations of the colitis.

4 Week Results

By the 4 week time point the animals with TNBs colitis receiving vehicle were largely recovered and it appeared that the colitis had resolved itself spontaneously.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

---

We claim:

1. A method of treating Crohn's Disease in a subject comprising administering to the subject a therapeutic amount of a linear or cyclic peptide of General Formula 2:

X—Ser—Thr—Thr—Thr—Asn—Tyr—Y (General Formula 2) (SEQ ID NO: 4)

wherein X is an amino acid terminal residue selected from Ala and D—Ala and Y is a carboxy terminal residue selected from Met, Thr and Thr-amide, or a pharmaceutically acceptable salt thereof.

2. A method as claimed in claim 1 in which the peptide is administered as a composition in conjunction with a pharmaceutically acceptable carrier.

3. A method as claimed in claim 1 in which the peptide is linear.

4. A method of treating Crohn's Disease in a subject comprising administering to the subject a therapeutic amount of a peptide selected from the group consisting of:

1. D—Ala—Ser—Thr—Thr—Thr—Asn—Tyr—Thr—NH$_2$
2. Ala—Ser—Thr—Thr—Thr—Asn—Tyr—Thr (SEQ ID NO: 6)
3. D—Ala—Ser—Thr—Thr—Thr—Asn—Tyr—Thr
4. D—Ala—Ala—Ser—Ser—Ser—Asn—Tyr—Met
5. Thr—Asp—Asn—Tyr—Thr (SEQ ID NO: 7)
6. Thr—Thr—Ser—Tyr—Thr (SEQ ID NO: 8)
7. Thr—Thr—Asn—Tyr—Thr (SEQ ID NO: 3)
8. D—Thr—Thr—Tyr—D—Thr
9. D—Ala—Ser—D—Thr—Thr—D—Thr—Asn—Tyr—D—Thr—NH$_2$
10. D—Ser—Ser—D—Thr—Thr—D—Thr—Thr—Tyr—D—Thr—NH$_2$.

5. A method as claimed in any one of claims 1 to 4 in which one more of the amino acids in the peptide is a substituted N-alkyl amino acid.

6. A method as claimed in claim 5, wherein said alkyl group contains 1 to 4 carbon atoms.

7. A method as claimed in any one of claims 1 to 4 in which the hydroxyl group side chains of one or more of the amino acids Ser, Thr, and/or Tyr is derivatised into an ether or ester group.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:1:

Ala  Ser  Thr  Thr  Thr  Asn  Tyr  Thr
    1                       5

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( i x ) FEATURE:
    ( A ) NAME/KEY: Peptide
    ( B ) LOCATION: 1..10
    ( D ) OTHER INFORMATION: /product="OTHER"
        / note= "Xaa at position 1 = C or absent (abs), 2 or 3 =
        A,G,V,S,T or abs, 4=S,T or abs, 5 = S,T,N,E,R,I,L or abs,
        6 = S,T,D or abs, 7 = T,S,N,R,Q,K,W or abs, 8 =
        Y,F,W,L,M,I or abs, 9 = T,R,G,M,M(0),C,T,G or abs, and
        10 = C or absent"

( x i ) SEQUENCE DESCRIPTION: SEQ ID NO:2:

Xaa Xaa Xaa Xaa Xaa Xaa Xaa Xaa Xaa Xaa
1               5                       10

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:3:

Thr Thr Asn Tyr Thr
1               5

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /product="OTHER"
            / note= "Xaa at position 1 is Ala or D-Ala and Xaa at
            position 8 is Met, Thr or Thr-amide"

( x i ) SEQUENCE DESCRIPTION: SEQ ID NO:4:

Xaa Ser Thr Thr Thr Asn Tyr Xaa
1               5

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:5:

Ser Thr Thr Thr Asn Tyr
1               5

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear

```
( i i ) MOLECULE TYPE: peptide ( x i ) SEQUENCE DESCRIPTION: SEQ ID NO:6:

Ala  Ser  Thr  Thr  Thr  Asn  Tyr  Thr
    1              5

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:7:

Thr  Asp  Asn  Tyr  Thr
    1              5

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:8:

Thr  Thr  Ser  Tyr  Thr
    1              5
```